(12) United States Patent
Ritter

(10) Patent No.: US 8,260,021 B2
(45) Date of Patent: Sep. 4, 2012

(54) METHOD FOR CORRECTION OF DISTORTION IN IMAGE DATA RECORDS RECORDED BY MEANS OF A MAGNETIC RESONANCE SCANNER, AS WELL AS A COMPUTER PROGRAM, IMAGE PROCESSING UNIT AND MAGNETIC RESONANCE SCANNER FOR CARRYING OUT THE METHOD

(75) Inventor: Dieter Ritter, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 1062 days.

(21) Appl. No.: 12/219,270

(22) Filed: Jul. 18, 2008

(65) Prior Publication Data

US 2009/0022384 A1 Jan. 22, 2009

(30) Foreign Application Priority Data

Jul. 20, 2007 (DE) .......................... 10 2007 033 880

(51) Int. Cl.
*A61B 5/055* (2006.01)
*G01R 33/565* (2006.01)
(52) U.S. Cl. ....................................................... 382/131
(58) Field of Classification Search .................. 382/128, 382/131; 250/363.07
See application file for complete search history.

(56) References Cited

U.S. PATENT DOCUMENTS

| | | | |
|---|---|---|---|
| 4,585,992 A | 4/1986 | Maudsley et al. | |
| 4,661,775 A | 4/1987 | Kormos et al. | |
| 4,720,679 A * | 1/1988 | Patrick et al. | 324/309 |
| 4,970,457 A | 11/1990 | Kaufman et al. | |
| 5,581,184 A | 12/1996 | Heid | |
| 5,823,959 A | 10/1998 | Rasche | |
| 5,886,524 A | 3/1999 | Krieg | |
| 6,150,815 A | 11/2000 | Janzen et al. | |
| 6,252,401 B1 | 6/2001 | Werthner et al. | |
| 2002/0048340 A1 | 4/2002 | Schaeffter et al. | |
| 2004/0032261 A1 | 2/2004 | Burkhardt | |
| 2005/0035763 A1 | 2/2005 | Canda et al. | |

(Continued)

FOREIGN PATENT DOCUMENTS

DE 4445782 7/1996

(Continued)

OTHER PUBLICATIONS

Jezzard et al (Correction for Geometric Distortion in Echo Planar Images from B0 Field Variations, Magnetic Resonance in Medicine 34, 1995, pp. 65-73.).*

(Continued)

*Primary Examiner* — Clayton E Laballe
*Assistant Examiner* — Leon W Rhodes, Jr.
(74) *Attorney, Agent, or Firm* — Harness, Dickey & Pierce, P.L.C.

(57) ABSTRACT

A method is disclosed which calculates local shifts of image elements in a loaded image data record which has been recorded by a magnetic resonance scanner using known recording parameters. In at least one embodiment, the known recording parameters and known local discrepancies of a basic magnetic field of the magnetic resonance scanner in a measurement volume of the magnetic resonance scanner are used to calculate the local shifts. A corrected image data record is created on the basis of the calculated shifts and the loaded image data record. This corrected image data record is finally displayed and/or stored. Furthermore, a computer program, an image processing unit and a magnetic resonance scanner for carrying out the method are disclosed.

18 Claims, 1 Drawing Sheet

U.S. PATENT DOCUMENTS

| | | | |
|---|---|---|---|
| 2005/0099504 A1* | 5/2005 | Nayar et al. | 348/222.1 |
| 2007/0018645 A1 | 1/2007 | Doddrell | |
| 2007/0142723 A1 | 6/2007 | Leach | |
| 2008/0068012 A1 | 3/2008 | Werthner | |
| 2008/0285835 A1 | 11/2008 | Holland et al. | |
| 2009/0021258 A1 | 1/2009 | Ritter | |
| 2009/0022385 A1 | 1/2009 | Ritter | |

FOREIGN PATENT DOCUMENTS

| | | |
|---|---|---|
| DE | 198 29 850 | 6/2000 |
| DE | 195 40 837 | 9/2004 |
| DE | 10337241 | 3/2005 |
| DE | 102006033248 | 1/2008 |
| EP | 0391515 | 10/1990 |
| EP | 1209481 | 5/2002 |
| WO | WO 95/30908 | 11/1995 |

OTHER PUBLICATIONS

German Office Action dated Feb. 16, 2009.

Skare, Andersson: "Correction of MR Image Distortions Induced by Metallic Objects Using a 3D Cubic B-Spline Basis Set: Application to Stereotactic Surgical Planning" in Magnetic Resonance in Medicine 54:169-181 (2005); Magazine.

U.S. Office Action for corresponding U.S. Appl. No. 12/219,275 dated Oct. 11, 2011.

Rueckert, D. et al.; Nonrigid Registration Using Free-Form Deformations: Application to Breast MR Images; IEEE Transactions on Medical Imaging, vol. 18, No. 8, Aug. 1999; 8; Others;1999.

Rohlfing, Torsten; Multimodale Datenfusion für die bildgesteuerte Neurochiurgie und Strahlentherapie; Dissertation; Berlin; Others; 2000.

Lee, S. et al.; Scattered Data Interpolation with Multilevel B-Splines; IEEE Transactions on Visualization and Computer Graphics, vol. 3, No. 3, Jul.-Sep. 1997; 3; Magazine; 1997.

Seim, Heiko; Automatische Registrierung mittels Mutual-Information am Beispiel von Schädel-CT-und MR-Datensätzen; Otto-von-Guericke-Universität Magdeburg; Praktikumsbericht Apr. 13, 2004-Sep. 10, 2004; Magdeburg; Others; 2004.

U.S. Office Action for corresponding U.S. Appl. No. 12/218,708 dated Oct. 16, 2009.

U.S. Office Action for corresponding U.S. Appl. No. 12/218,708 dated Apr. 5, 2010.

* cited by examiner

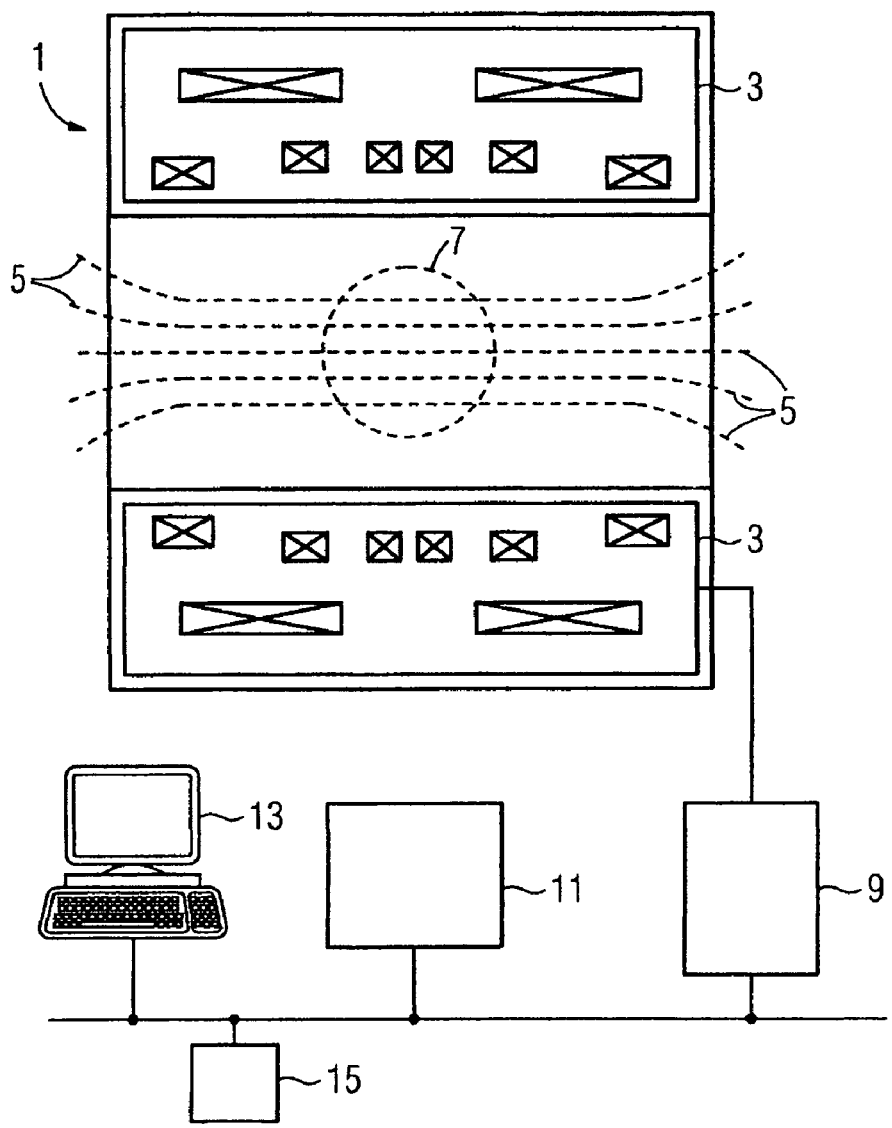
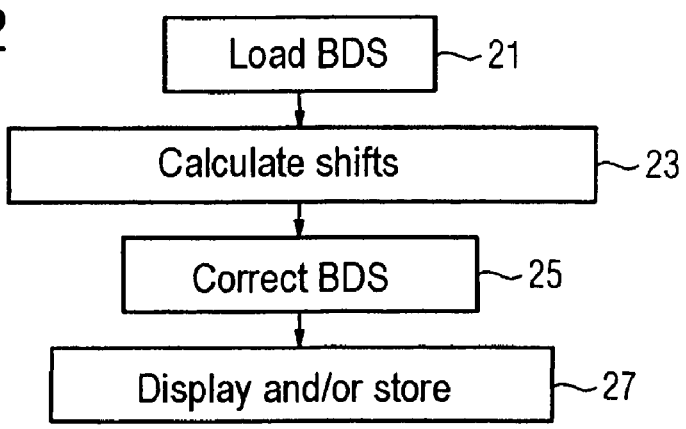

METHOD FOR CORRECTION OF DISTORTION IN IMAGE DATA RECORDS RECORDED BY MEANS OF A MAGNETIC RESONANCE SCANNER, AS WELL AS A COMPUTER PROGRAM, IMAGE PROCESSING UNIT AND MAGNETIC RESONANCE SCANNER FOR CARRYING OUT THE METHOD

PRIORITY STATEMENT

The present application hereby claims priority under 35 U.S.C. §119 on German patent application number DE 10 2007 033 880.7 filed Jul. 20, 2007, the entire contents of which is hereby incorporated herein by reference.

FIELD

Embodiments of the invention generally relate to a method for correction of distortion in image data records recorded by means of a magnetic resonance scanner.

Embodiments of the invention likewise relate to a computer program, to an image processing unit and/or to a magnetic resonance scanner for carrying out the method.

BACKGROUND

Magnetic resonance is a known technique by which images of the interior of an examination object can be produced. In this case, the relationship between the precession frequencies (Larmor frequencies) of excited spins and the magnetic field strength of the magnetic field in the magnetic resonance scanner is used for position resolution. The magnetic field that is used is in this case composed of the basic magnetic field of the magnetic resonance scanner and applied gradient magnetic fields. Normal methods for reconstruction of image data records from magnetic resonance signals are predicated on a homogeneous basic magnetic field and strictly linear gradient magnetic fields.

The relationship between the Larmor frequencies and the magnetic field that is used results in geometric distortion along the frequency coding direction (read direction) in the image data records obtained from the magnetic resonance signals, if there are any inhomogeneities in the basic magnetic field. If there are non-linearities in the gradient fields, the distortion occurs not only on the tomographic image plane but also at right angles to this in the case of slice stimuli with a selection gradient. In practice, such inhomogeneities in the basic magnetic field and non-linearities in the gradient fields cannot be avoided completely. Nevertheless, the discrepancies in the basic magnetic field, that is to say the inhomogeneity, within a measurement volume of a magnetic resonance scanner should be less than three parts per million (ppm).

The resultant distortion in this case relates not only to the geometric position of the image data reconstructed from the magnetic resonance signals, but also to the reconstructed image signal strength. Attenuation of the image signal strength can occur in this case, for example, by dephasing of the spins in the presence of strong local basic field inhomogeneities. Further corrupting changes in the image signal strength are possible as a result of the spatial distribution of the intensity values, determined from the magnetic resonance signals, on an area whose size differs from the actual area.

The reasons why inhomogeneities occur in basic magnetic fields in magnetic resonance scanners are, for example, linked to the design, that is to say they are dependent, for example, on the design and winding geometry of the basic field magnet, the shielding and any shim apparatuses that are present. Inhomogeneities in the basic magnetic field caused in this way are static, that is to say they remain essentially constant over time.

In order to determine the inhomogeneity of the basic magnetic field, the magnetic field which actually occurs, for example, is measured at a plurality of measurement points on the surface of the measurement volume with the aid of magnetic field sensors, for example Hall sensors, of the measurement phantom.

If the measurement points lie on a spherical surface with a radius $r_0$, the coefficients $A_{l,m}$ and $B_{l,m}$, which are also referred to as a "spectrum" of the following development function can be calculated using spherical functions of magnetic fields. Using said development function:

$$B0(r, \vartheta, \varphi) = \sum_{l=0}^{\infty} \left(\frac{r}{r_0}\right)^l \sum_{m=0}^{l} P_{l,m}(\cos\vartheta)(A_{l,m}\cos(m\varphi) + B_{l,m}\sin(m\varphi))$$

the total basic magnetic field B0 can then be calculated from this at any point $(r,\upsilon,\phi)$ (spherical coordinates) within the measurement volume. $P_{l,m}$ in this case denotes the normalized Legendré functions associated with the Legendré polynomials $P_l$.

Any local discrepancy of the basic magnetic field $\Delta_{B0}(r,\upsilon,\phi)=B0(r,\upsilon,\phi)-B0_{nom}$ can be calculated from the calculated values $B0(r,\upsilon,\phi)$ and the nominal value for the basic magnetic field $B0_{nom}$.

The basic field inhomogeneity can also be calculated as the relative basic field inhomogeneity $\delta_{B0}$ at any point $(r,\upsilon,\phi)$:

$$\delta_{B0}(r, \vartheta, \varphi) = \frac{B0(r, \vartheta, \varphi) - B0_{nom}}{B0_{nom}} = \frac{\Delta_{B0}(r, \vartheta, \varphi)}{B0_{nom}}$$

The distribution of the relative basic field inhomogeneity can be stored on a position-resolved basis in a so-called B0 map. A B0 map such as this may, for example, be represented as a height profile on a slice plane through the measurement volume. In this case, the height profile indicates the relative basic field inhomogeneity at the respective location in the measurement volume.

Further reasons for inhomogeneities of a magnetic field in a magnetic resonance scanner are, for example, susceptibility changes caused by an examination object being introduced into the magnetic resonance scanner, dynamic disturbances caused by eddy currents or artefacts such as "chemical shift", liquid artefacts or movements of the examination object. Inhomogeneities caused in this way depend on the respective situation, for example the nature of the examination and of the examination object.

All types of distortion in image data records are undesirable, in particular in medical image data records, since they corrupt a diagnosis, or at least make it harder and, for example, make it harder to determine the absolute position of a lesion. Because of the various possible causes and types of distortion, various methods already exist to correct for the various types of distortion in image data records.

One method for distortion correction for gradient non-linearities in magnetic resonance scanners is known from DE 195 40 837 B4. In this case, two auxiliary data records which describe a shift of a measured point with respect to an actual point of a signal origin are used to carry out position corrections in the x and y directions. Intensity corrections are also used, in addition to the position corrections.

DE 198 29 850 C2 describes a method for reconstruction of a planar slice image from magnetic resonance signals in inhomogeneous magnetic fields. In this case, image elements of a planar slice image are produced from a plurality of original image elements on curved slices in the examination object.

WO 95/30908 A1 describes a method in which a generalized Fresnel transformation (GFT reconstruction) is carried out in the read direction. The GFT reconstruction takes account of any known position dependency of the main magnetic field in the read direction in order to allow distortion and intensity errors to be corrected for during the transformation from the measurement data space (k space) to the position space.

There is also a requirement for powerful methods for correction for distortion in image data records recorded by means of magnetic resonancing.

SUMMARY

At least one embodiment of the invention makes it possible, in a simple and at the same time effective manner, to correct for distortion in image data records recorded by way of a magnetic resonance scanner.

To this end, the method according to at least one embodiment of the invention calculates local shifts of image elements in a loaded image data record which has been recorded using known recording parameters in a measurement volume of a magnetic resonance scanner. In this case, the known recording parameters and known local discrepancies of a basic magnetic field of the magnetic resonance scanner in the measurement volume of the magnetic resonance scanner are used to calculate the local shifts. A corrected image data record is created on the basis of the calculated shifts and the loaded image data record. This corrected image data record is finally displayed and/or stored.

The method according to at least one embodiment of the invention can be implemented easily and can also easily be integrated in any algorithms which may already exist for distortion correction. Further advantages are the rapidity of the correction calculation associated with this, on the one hand, because the calculation is intrinsically carried out quickly, and on the other hand because there is no need for multiple measurements. The measurement for recording the image data record and the knowledge about the local discrepancies of the basic magnetic field are sufficient. The local discrepancies of the basic magnetic field are generally determined in a standard form while a magnetic resonance scanner is being set up. This determination of the local discrepancies and therefore a basis for the method are based on physical measurements, and are therefore independent of image interpretation errors.

Furthermore, at least one embodiment is directed to a computer program, an image processing unit and/or a magnetic resonance scanner, for carrying out the method.

BRIEF DESCRIPTION OF THE DRAWINGS

Further advantages and details of the present invention will become evident from the example embodiments described in the following text, and from the drawings. The described examples do not represent any restriction to the invention. In the figures:

FIG. 1 shows a schematic layout of a magnetic resonance scanner,

FIG. 2 shows a schematic flowchart of the method according to an embodiment of the invention.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region layer, or section without departing from the teachings of the present invention.

FIG. 1 shows, schematically, a side view of the layout of a magnetic resonance scanner 1. Only those parts which are significant to embodiments of the invention are illustrated in this case. Further parts, such as a couch, local coils, gradient coils and units for controlling them, are adequately known from the prior art and are not illustrated, for the sake of clarity.

In particular, the magnetic resonance scanner 1 has a supraconducting basic field magnet 3. The basic field magnet 3, normally a cryogenic magnet 3 with an opening in the form of a tunnel, and an open magnet, produces a strong basic magnetic field (represented by exemplary field lines sketched by dashed lines), which is normally between 0.2 Tesla and 3 Tesla or more. The basic magnetic field 5 is homogeneous in a measurement volume 7 of the magnetic resonance scanner 1 except for relatively minor local discrepancies from a nominal value.

In order to examine an object by way of magnetic resonance imaging, various magnetic fields which are matched to one another as accurately as possible in terms of their time and spatial characteristics are applied to the body. The magnetic resonance signals produced in this way are measured as measurement data.

An object to be examined is placed on a couch (not illustrated here) and is positioned in the measurement volume 7 in order to record measurement data.

A control unit 9 controls the magnetic resonance scanner, in particular during the acquisition of the measurement data.

An image processing unit 11 uses the measurement data to produce an image data record, which is displayed to a user via a control console 13, or is stored in a memory unit 15.

The image processing unit 11 is in this case designed such that the method according to an embodiment of the invention can be carried out using the image processing unit 11, if appropriate together with the control unit 9. For this purpose, for example, a computer program according to an embodiment of the invention is installed in the image processing unit 11 and/or the control unit 9 such that it can be run.

An image processing unit 11 which is designed to carry out the method according to an embodiment of the invention may, however, also be operated independently of a magnetic resonance scanner 1.

FIG. 2 shows a schematic flow chart of the method according to an embodiment of the invention.

In this case, first of all, an image data record (BDS for short) which has been recorded by the magnetic resonance scanner using known recording parameters is loaded, for example, on a control console or an image processing unit (block 21).

Local shifts of image elements along the read direction in the image data record are calculated, for example in the following way (block 23), from known local discrepancies of the basic magnetic field of the magnetic resonance scanner which had been determined, for example, in the manner described above, and the known recording parameters for the image data record:

The local shifts in the read direction (frequency coding direction) $\Delta_{ro}^{B0}(r,\upsilon,\phi)$ are given, as a function of the gradient strength of the frequency coding gradient $G_{ro}$ by:

$$\Delta_{ro}^{B0}(r, \vartheta, \varphi) = \frac{\Delta_{B0}(r, \vartheta, \varphi)}{G_{ro}} = \frac{\delta_{B0}(r, \vartheta, \varphi) * B0}{G_{ro}},$$

where $\Delta_{B0}(r,\upsilon,\phi) = B0(r,\upsilon,\phi) - B0_{nom}$ is the local discrepancy of the basic magnetic field, and $\delta_{B0}(r,\upsilon,\phi)$ is the relative basic field inhomogeneity at the point $(r,\upsilon,\phi)$.

In this case, of course, only shifts at points $(r,\upsilon,\phi)$ which are part of the loaded image data record need be calculated.

The gradient strength $G_{ro}$ can in this case be calculated, for example, from the known recording parameters such as the pixel bandwidth (pbw), the resolution (pix) and image field of view ($x_{FoV}$, FoV: "field of view") and the gyromagnetic ratio $\gamma^*$ of protons:

$$G_{ro} = \frac{pbw * pix}{\gamma^* * x_{FoV}}.$$

A corrected image data record is created (block 25) on the basis of the calculated shifts in the image data record.

In this case, image elements in the image data record are corrected in accordance with the calculated local shifts, that is to say each image element is shifted corresponding to the calculated shifts so as to compensate for distortion that has resulted from the inhomogeneity of the basic magnetic field, along the read direction.

The shifted image elements generally do not coincide exactly with a corresponding image element in the corrected image data record, which comprises regularly distributed image elements. It is therefore worthwhile carrying out an intensity interpolation process in order to determine the intensity values of each regularly distributed image, element in the image data record, in order to avoid a deterioration in the resolution of the corrected image data record.

This can be done by a linear intensity interpolation process or a so-called "nearest neighbor" interpolation process. Both methods are adequately known from the prior art. However, the use of one of these methods can lead to the resolution of the corrected image data record becoming coarser.

A so-called B-spline method is proposed for an intensity interpolation process that is as accurate as possible. B-spline methods are also already known from the prior art.

In this case, for example in the case of a two-dimensional B-spline interpolation process, the intensity $I^T$ is determined at a pixel $(x_p, y_p)$ which corresponds to an image element in the corrected image data record, by means of the basic functions $B_m(u)$ and $B_n(v)$ and the intensities $I(x_{i+m-1}, y_{j+n-1})$ at surrounding pixels $(x_{i+m-1}, y_{j+n-1})$, which correspond to the original, shifted image elements, as follows:

$$I^T(x_p, y_p) = \sum_{m=0}^{3} \sum_{n=0}^{3} B_m(u) B_n(v) I(x_{i+m-1}, y_{j+n-1}),$$

where:

$i = \lfloor x_p \rfloor;\quad u = x_p - \lfloor x_p \rfloor;\quad B_0(t) = (-t^3 + 3t^2 - 3t + 1)/6;$ $j = \lfloor y_p \rfloor;\quad v = y_p - \lfloor y_p \rfloor;\quad B_1(t) = (3t^3 - 6t^2 + 4)/6;$ $B_2(t) = (-3t^3 + 3t^2 + 3t + 1)/6;$ $B_3(t) = t^3/6.$ Finally, the corrected image data record is displayed, for example on a display unit on the control console, and/or is stored, for example in a memory unit.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for correction of distortion in image data records which are recorded via a magnetic resonance scanner, wherein the magnetic resonance scanner has a measurement volume in which there is a basic magnetic field which has local discrepancies from a nominal value, comprising:

determining the local discrepancies based on locations on a surface of the measurement volume and a development function;

loading an image data record, recorded by the magnetic resonance scanner using known recording parameters;

calculating local shifts of image elements in the loaded image data record from the local discrepancies of the basic magnetic field and the known recording parameters;

creating a corrected image data record on the basis of the calculated local shifts and the loaded image data record; and at least one of displaying and storing the corrected image data record.

2. The method as claimed in claim 1, wherein the recording parameters comprise values for a pixel bandwidth that is used, a resolution that is used, an image area that is used, and a gyromagnetic ratio.

3. The method as claimed in claim 1, wherein a value of a frequency coding gradient is calculateable from the recording parameters.

4. The method as claimed in claim 3, wherein the local shift is calculated in the direction of the frequency coding gradient.

5. The method as claimed in claim 1, wherein the correction of the recorded image data record comprises an intensity interpolation process.

6. The method as claimed in claim 5, wherein the intensity interpolation process is carried out via a B-spline method.

7. The method as claimed in claim 1, wherein the local shift is calculated from the quotient of the local discrepancy between the basic magnetic field of the magnetic resonance scanner and the nominal value, and a value of the frequency coding gradient.

8. The method as claimed in claim 1, wherein the correction comprises back-shifting of image elements of the loaded image data record using the calculated local shifts.

9. A computer program embodied on a non-transitory computer readable medium configured to implement the method as claimed in claim 1 on the computater, when the computer program is run on the computater.

10. An image processing unit, designed to carry out the method as claimed in claim 1.

11. A magnetic resonance scanner, comprising:
an image processing unit, designed to carry out the method as claimed in claim 1.

12. The method as claimed in claim 2, wherein a value of a frequency coding gradient is calculateable from the recording parameters.

13. The method as claimed in claim 12, wherein the local shift is calculated in the direction of the frequency coding gradient.

14. The method as claimed in claim 2, wherein the correction of the recorded image data record comprises an intensity interpolation process.

15. The method as claimed in claim 14, wherein the intensity interpolation process is carried out via a B-spline method.

16. An image processing unit for correction of distortion in image data records which are recorded via a magnetic resonance scanner, wherein the magnetic resonance scanner has a measurement volume in which there is a basic magnetic field which has local discrepancies from a nominal value, comprising:

means for determining the local discrepancies based on locations on a surface of the measurement volume and a development function;

means for loading an image data record, recorded by the magnetic resonance scanner using known recording parameters;

means for calculating local shifts of image elements in the loaded image data record from the local discrepancies of the basic magnetic field and the known recording parameters;

means for creating a corrected image data record on the basis of the calculated local shifts and the loaded image data record; and means for at least one of displaying and storing the corrected image data record.

17. A magnetic resonance scanner, comprising:
an image processing unit as claimed in claim 16.

18. A non-transitory computer readable medium including program segments for, when executed on a computer device, causing the computer device to implement the method of claim 1.

* * * * *